United States Patent
Wang et al.

(10) Patent No.: US 12,023,654 B2
(45) Date of Patent: Jul. 2, 2024

(54) CATALYST AND METHOD FOR PREPARATION OF 2-ETHOXYPHENOL BY CATALYTIC DEPOLYMERIZATION OF LIGNIN

(71) Applicant: Anhui University of Science & Technology, Huainan (CN)

(72) Inventors: Yishuang Wang, Huainan (CN); Mingqiang Chen, Huainan (CN); Jingjing Shi, Huainan (CN); Zhiyuan Tang, Huainan (CN); Zhonglian Yang, Huainan (CN); Jun Wang, Huainan (CN); Han Zhang, Huainan (CN)

(73) Assignee: Anhui University of Science & Technology, Huainan (CN)

( * ) Notice: Subject to any disclaimer, the term of this patent is extended or adjusted under 35 U.S.C. 154(b) by 506 days.

(21) Appl. No.: 17/240,546

(22) Filed: Apr. 26, 2021

(65) Prior Publication Data
US 2022/0062872 A1 Mar. 3, 2022

(30) Foreign Application Priority Data
Aug. 27, 2020 (CN) .......................... 202010879852.8

(51) Int. Cl.
| | | |
|---|---|---|
| *C07C 41/01* | (2006.01) | |
| *B01J 19/14* | (2006.01) | |
| *B01J 21/14* | (2006.01) | |
| *B01J 23/888* | (2006.01) | |
| *B01J 37/00* | (2006.01) | |
| *B01J 37/02* | (2006.01) | |
| *B01J 37/08* | (2006.01) | |

(52) U.S. Cl.
CPC .......... *B01J 23/8885* (2013.01); *B01J 19/14* (2013.01); *B01J 21/14* (2013.01); *B01J 37/0036* (2013.01); *B01J 37/009* (2013.01); *B01J 37/024* (2013.01); *B01J 37/082* (2013.01); *C07C 41/01* (2013.01); *B01J 2219/00189* (2013.01)

(58) Field of Classification Search
CPC combination set(s) only.
See application file for complete search history.

(56) References Cited

U.S. PATENT DOCUMENTS

| | | | | |
|---|---|---|---|---|
| 4,647,704 | A | 3/1987 | Engel et al. | |
| 6,565,643 | B2* | 5/2003 | Nieman | B01J 21/16 |
| | | | | 423/325 |
| 2015/0307418 | A1* | 10/2015 | Frey | C07C 5/373 |
| | | | | 422/187 |

FOREIGN PATENT DOCUMENTS

| | | | |
|---|---|---|---|
| CN | 1701848 A | * 11/2005 | |
| CN | 1701848 A | 11/2005 | |
| WO | WO-2017084907 A1 | * 5/2017 | C07C 29/132 |

OTHER PUBLICATIONS

Page 1 of PubChem for Nickel nitrate obtained Feb. 12, 2024 (Year: 2024).*
Page 1 of PubChem for Ammonium tungstate (VI) obtained Feb. 12, 2024 (Year: 2024).*
Page 1 of PubChem for Ammonium molybdate obtained Feb. 12, 2024 (Year: 2024).*
Mar. 24, 2022—(CN) First Office Action—App. No. 202010879852.8.
Jun. 15, 2022—(CN) Second Office Action—App. No. 202010879852.8.
Zhiyuan Tang, et al., "Study of Mo-based sepiolite catalyst on depolymerization of lignin under supercritical ethanol", Int J Energy Res 2019; 1-12, wileyonlinelibrary.com/journal/er, pp. 12.

* cited by examiner

*Primary Examiner* — Rosalynd A Keys
(74) *Attorney, Agent, or Firm* — Banner & Witcoff, Ltd.

(57) ABSTRACT

The present disclosure discloses a catalyst and a method for preparing 2-ethoxyphenol by catalytic depolymerization of lignin. The catalyst comprises sepiolite as a carrier and tungsten, nickel and molybdenum as active components supported on sepiolite. The catalyst for preparing 2-ethoxyphenol by catalytic depolymerization of lignin in the present disclosure can catalytically depolymerize lignin, realize the directional preparation of 2-ethoxyphenol from lignin, and co-produce lignin oil. It has a comparatively high selectivity for 2-ethoxyphenol and can achieve a lignin conversion rate of more than 95%, a 2-ethoxyphenol selectivity of more than 20% in a liquid product, and a yield of more than 100 mg/g of lignin.

6 Claims, 3 Drawing Sheets

CATALYST AND METHOD FOR PREPARATION OF 2-ETHOXYPHENOL BY CATALYTIC DEPOLYMERIZATION OF LIGNIN

CROSS REFERENCE TO RELATED APPLICATIONS

The present application claims foreign priority to Chinese Patent Application No. 202010879852.8, filed Aug. 27, 2020, the disclosure of which is incorporated herein by reference in its entirety.

TECHNICAL FIELD

The present disclosure relates to the field of catalytic depolymerization of lignin, in particular to a catalyst and a method for preparing 2-ethoxyphenol by catalytic depolymerization of lignin.

BACKGROUND

Ethoxyphenol is an important organic chemical product and a pharmaceutical raw material, and 2-ethoxyphenol is used as the raw material to synthesize ethyl vanillin fragrances. Their source, synthesis and preparation have always been research hotspots in the field of organic chemistry. At present, organic synthesis methods for the synthesis of 2-ethoxyphenol at home and abroad have many factors that are difficult to control. In addition, the demanding operating conditions as well as the expensive process routes and raw materials also bring a series of difficulties to the synthesis.

Lignin is a natural biomass which is second-largest in content and highest in utilization ratio, and it is a class of organic polymer compounds naturally with an aromatic ring structure. Lignin is mainly composed of three basic structural units, which are syringyl propane, guaiacyl propane and p-hydroxyphenyl propane, respectively. They are linked together by a disordered combination of monomer dehydrogenation polymerization, C—C bond, C—O bond, etc. If 2-ethoxyphenol can be obtained by depolymerization from lignin as the raw material, it can solve the existing problem that the synthesis of 2-ethoxyphenol is difficult.

SUMMARY

The technical problem to be solved by the present disclosure is to provide a catalyst and a method for preparing 2-ethoxyphenol by catalytic depolymerization of lignin.

In order to solve the above technical problem, the present disclosure uses the following technical solution: a catalyst for preparing 2-ethoxyphenol by catalytic depolymerization of lignin comprising sepiolite as a carrier and tungsten, nickel and molybdenum as active components supported on sepiolite.

Further, the total content of tungsten, nickel and molybdenum is 20 to 40 wt %. In such a design, the total content of the active components is 20 to 40 wt %, which not only obtains enough catalytic active sites but also avoids the transitional coverage of the catalytic active sites on the sepiolite carrier.

Further, the molar ratio of tungsten, nickel and molybdenum is 1:1:1. In such a design, each metal is evenly distributed on the surface of the carrier, which makes sure that the catalyst has a comparatively high specific surface area and provides sufficient active sites.

Further, a method for its preparation comprises the following steps: selecting a precursor salt of tungsten, a precursor salt of nickel, and a precursor salt of molybdenum; and loading tungsten, nickel and molybdenum on sepiolite by a stepwise impregnation method in the order of tungsten impregnation, nickel impregnation and molybdenum impregnation to obtain the catalyst for preparing 2-ethoxyphenol by catalytic depolymerization of lignin. In the process of implementing the present disclosure, the inventors have found in pretests that when the three metals are impregnated at the same time, there are interactions between the metal precursor salts, which cause the catalyst to exhibit a comparatively low activity. In order to avoid this phenomenon, a stepwise impregnation method is used, which can successfully introduce the respective metal sites.

Further, a hydrothermal assistant aging treatment is used in the impregnation treatment process. The hydrothermal assistant aging treatment is an airtight and constant-temperature treatment in a high-pressure hydrothermal synthesis kettle, and the treatment is carried out under conditions of $N_2$ atmosphere, 80 to 180° C., and 12 to 24 hours. The hydrothermal assistant aging treatment can improve the stability of the catalyst, allow for recycling, and comply with the idea of green chemistry.

A method for preparing 2-ethoxyphenol by catalytic depolymerization of lignin comprises the following steps: using ethanol as a reaction medium; adding lignin and the above catalyst; and performing the reaction in a $N_2$ atmosphere.

Further, lignin, catalyst and ethanol are fed in a mass ratio of 0.8 to 1.2:0.3 to 0.7:28 to 32. Under this feeding ratio, it not only allows the lignin to be sufficiently dissolved in the ethanol solvent, but also guarantees sufficient contact between the catalyst and the lignin molecules, which leads to a higher reaction rate, makes the reaction more complete, and avoids a surplus of reactants and waste of catalyst.

Further, the reaction conditions include a temperature of 260 to 300° C., a pressure of 6.2 to 9.5 MPa, a stirring rate of 350 to 550 r/min, and time of 1 to 5 hours. Such reaction conditions are conducive to the formation of a supercritical system, and under this system, lignin has better solubility and diffusibility, which facilitates the proceeding of the reaction.

The beneficial effects of the present disclosure include the following:

The catalyst for preparing 2-ethoxyphenol by catalytic depolymerization of lignin in the present disclosure can catalytically depolymerize lignin, realize the directional preparation of 2-ethoxyphenol from lignin, and co-produce lignin oil. It has a comparatively high selectivity for 2-ethoxyphenol and can achieve a lignin conversion rate of more than 95%, a 2-ethoxyphenol selectivity of more than 20% in a liquid product, and a yield of more than 100 mg/g of lignin.

The catalyst for preparing 2-ethoxyphenol by catalytic depolymerization of lignin in the present disclosure is environmentally friendly, does not cause pollution, can be recycled and reused, and is a good green, efficient and economical catalyst.

The method for preparing 2-ethoxyphenol by catalytic depolymerization of lignin in the present disclosure avoids inconvenient operation, environmental pollution and resource waste in the existing preparation processes. It is simple to operate, highly safe, and highly feasible, and the catalyst can be reused, which complies with the idea of going green, and has a high selectivity for 2-ethoxyphenol.

DESCRIPTION OF THE EMBODIMENTS

Figure 1:
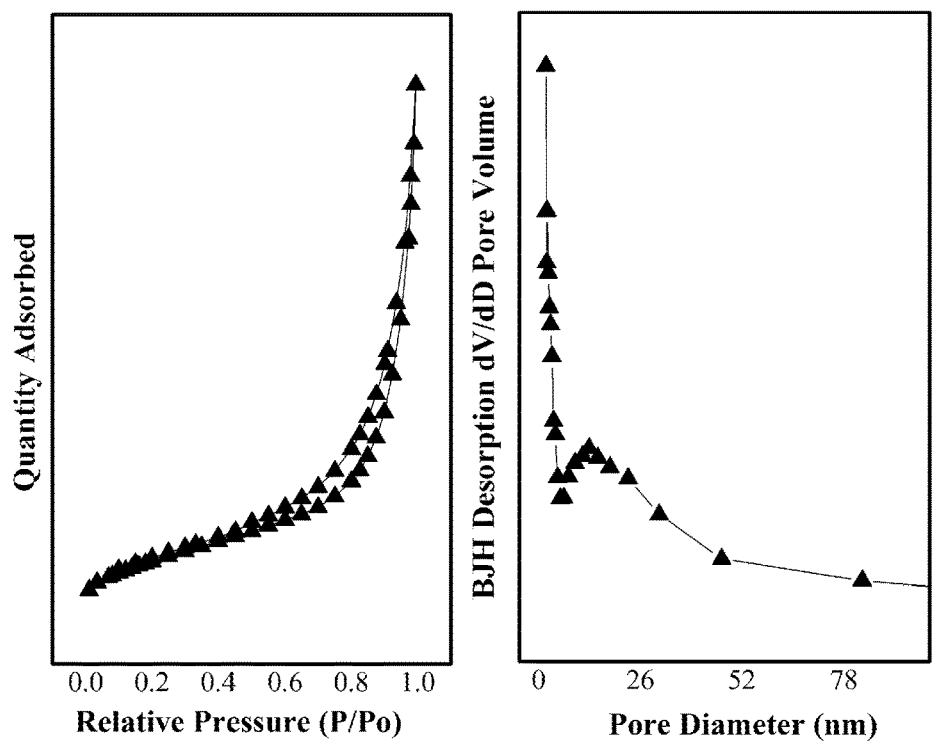
FIG. 1 is a diagram showing the $N_2$-adsorption-desorption isotherm and pore size distribution of the catalyst prepared in Example 2 of the present disclosure.

The present disclosure is further described hereinbelow in conjunction with examples:

The various raw materials used in the following examples, unless otherwise specified, are all commercially available products known in the art.

EXAMPLE 1

Pretreatment of Sepiolite

Sepiolite raw material was added to 5 mol/L nitric acid, magnetically stirred for 2 hours in a 80° C. thermostatic water bath, then filtered by suction, washed, dried, and mechanically pulverized to obtain solid powder I; the solid powder I was placed in a tube furnace, heated to 600° C. at a heating rate of 2° C./min, and then calcined in an air atmosphere for 4 hours to obtain purified sepiolite.

EXAMPLE 2

Preparation of a Catalyst and Catalytic Depolymerization of Lignin to 2-Ethoxyphenol 2.51 g of ammonium tungstate was completely dissolved in 100 ml of deionized water, and 5 g of sepiolite prepared in the example was added. After stirring evenly, the mixture was dispersed in an ultrasonic vibrator for 1 hour, subsequently treated in a hydrothermal synthesis kettle at 180° C. for 12 hours, dried by evaporation at 90° C., and then dried at 105° C. for 12 hours. Thereafter, the obtained solids were ground into powder, calcined in a tube furnace at 500° C. for 4 hours under an air atmosphere, and collected, the heating rate being 2° C./min. The collected solid powder was added to an aqueous solution of 1.74 g of nickel nitrate and treated in the same way. After collection, it was impregnated with 2.86 g of ammonium molybdate in the same way to obtain a catalyst for preparing 2-ethoxyphenol by catalytic depolymerization of lignin with a total content of 40 wt % of tungsten, nickel and molybdenum.

1.0042 g of alkali lignin and 0.5012 g of catalyst were placed in a 100 mL autoclave, and then 30 mL of anhydrous ethanol was added, and sufficiently mixed in an ultrasonic vibrator. Subsequently, 0.5 MPa high-purity nitrogen was introduced. Before reaction, the mixture was stirred for 15 minutes at 380 rpm, and then heated from 25° C. normal temperature to 260° C. at a temperature rising rate of 6° C./min, and the reaction was carried out at this temperature for 1 hour. After the reaction, the autoclave was quickly quenched in an ice water bath. After the temperature was lowered to normal temperature, the autoclave was opened and the reaction product was removed. The reaction product was first filtered with a sand core funnel to separate the solid and liquid phases, and the solid phase product was washed repeatedly with anhydrous ethanol solvent. After multiple washings, the solid phase product was removed, and dried in a drying oven at 105° C. for 12 hours. The liquid phase product was placed in a rotary evaporator and dried by evaporation in a 100 mL distillation flask under the conditions of 44° C. and 110 r/min (to remove the ethanol solvent and water phase) to obtain 2-ethoxyphenol and co-product lignin oil in liquid state. According to calculations, the conversion rate of lignin was 96%, the selectivity of 2-ethoxyphenol among the phenolic monomers in the liquid product was 25%, and the yield was 110 mg/g of lignin.

EXAMPLE 3

Preparation of a Catalyst and Catalytic Depolymerization of Lignin to 2-Ethoxyphenol 2.51 g of ammonium tungstate was completely dissolved in 100 ml of deionized water, and 5 g of sepiolite prepared in the example was added. After stirring evenly, the mixture was vibrated in an ultrasonic vibrator for 1 hour, subsequently treated in a hydrothermal synthesis kettle at 120° C. for 16 hours, dried by evaporation at 90° C., and then dried at 105° C. for 12 hours. Thereafter, the obtained solids were ground into powder, calcined in a tube furnace at 500° C. for 4 hours under an air atmosphere, and collected, the heating rate being 2° C./min. The collected solid powder was added to an aqueous solution of 1.74 g of nickel nitrate and treated in the same way. After collection, it was impregnated with 2.86 g of ammonium molybdate in the same way to obtain a catalyst for preparing 2-ethoxyphenol by catalytic depolymerization of lignin with a total content of 40 wt % of tungsten, nickel and molybdenum.

1.0037 g of alkali lignin and 0.5044 g of catalyst were placed in a 100 mL autoclave, and then 30 mL of anhydrous ethanol was added, and sufficiently mixed in an ultrasonic vibrator. Subsequently, 0.5 MPa high-purity nitrogen was introduced. Before reaction, the mixture was stirred for 15 minutes at 380 rpm, and then heated from 25° C. normal temperature to 280° C. at a temperature rising rate of 6° C./min, and the reaction was carried out at this temperature for 2 hours. After the reaction, the autoclave was quickly quenched in an ice water bath. After the temperature was lowered to normal temperature, the autoclave was opened and the reaction product was removed. The reaction product was first filtered with a sand core funnel to separate the solid and liquid phases, and the solid phase product was washed repeatedly with anhydrous ethanol solvent. After multiple washings, the solid phase product was removed, and dried in a drying oven at 105° C. for 12 hours. The liquid phase product was placed in a rotary evaporator and dried by evaporation in a 100 mL distillation flask under the conditions of 44° C. and 110 r/min (to remove the ethanol solvent and water phase) to obtain 2-ethoxyphenol and co-product lignin oil in liquid state. According to calculations, the conversion rate of lignin was 98%, the selectivity of 2-ethoxyphenol among the phenolic monomers in the liquid product was 27%, and the yield was 115 mg/g of lignin.

EXAMPLE 4

Preparation of a Catalyst and Catalytic Depolymerization of Lignin to 2-Ethoxyphenol 2.51 g of ammonium tungstate was completely dissolved in 100 ml of deionized water, and 5 g of sepiolite prepared in the example was added. After stirring evenly, the mixture was vibrated in an ultrasonic vibrator for 1 hour, subsequently treated in a hydrothermal synthesis kettle at 80° C. for 20 hours, dried by evaporation at 90° C., and then dried at 105° C. for 12 hours. Thereafter, the obtained solids were ground into powder, calcined in a tube furnace at 500° C. for 4 hours under an air atmosphere, and collected, the heating rate being 2° C./min. The collected solid powder was added to an aqueous solution of 1.74 g of nickel nitrate and treated in the same way. After collection, it was impregnated with 2.86 g of ammonium molybdate in the same way to obtain a catalyst for preparing 2-ethoxyphenol by catalytic depolymerization of lignin with a total content of 40 wt % of tungsten, nickel and molybdenum.

1.0021 g of alkali lignin and 0.5045 g of catalyst were placed in a 100 mL autoclave, and then 30 mL of anhydrous ethanol was added, and sufficiently mixed in an ultrasonic vibrator. Subsequently, 0.5 MPa high-purity nitrogen was introduced. Before reaction, the mixture was stirred for 15 minutes at 380 rpm, and then heated from 25° C. normal temperature to 300° C. at a temperature rising rate of 6° C./min, and the reaction was carried out at this temperature for 4 hours. After the reaction, the autoclave was quickly quenched in an ice water bath. After the temperature was lowered to normal temperature, the autoclave was opened and the reaction product was removed. The reaction product was first filtered with a sand core funnel to separate the solid and liquid phases, and the solid phase product was washed repeatedly with anhydrous ethanol solvent. After multiple washings, the solid phase product was removed, and dried in a drying oven at 105° C. for 12 hours. The liquid phase product was placed in a rotary evaporator and dried by evaporation in a 100 mL distillation flask under the conditions of 44° C. and 110 r/min (to remove the ethanol solvent and water phase) to obtain 2-ethoxyphenol and co-product lignin oil in liquid state. According to calculations, the conversion rate of lignin was 99%, the selectivity of 2-ethoxyphenol among the phenolic monomers in the liquid product was 28%, and the yield was 118 mg/g of lignin.

EXAMPLE 5

Preparation of a Catalyst and Catalytic Depolymerization of Lignin to 2-Ethoxyphenol 0.94 g of ammonium tungstate was completely dissolved in 100 ml of deionized water, and 5 g of sepiolite prepared in the example was added. After stirring evenly, the mixture was vibrated in an ultrasonic vibrator for 1 hour, subsequently treated in a hydrothermal synthesis kettle at 120° C. for 18 hours, dried by evaporation at 90° C., and then dried at 105° C. for 12 hours. Thereafter, the obtained solids were ground into powder, calcined in a tube furnace at 500° C. for 4 hours under an air atmosphere, and collected, the heating rate being 2° C./min. The collected solid powder was added to an aqueous solution of 1.07 g of nickel nitrate and treated in the same way. After collection, it was impregnated with 0.65 g of ammonium molybdate in the same way to obtain a catalyst for preparing 2-ethoxyphenol by catalytic depolymerization of lignin with a total content of 20 wt % of tungsten, nickel and molybdenum.

1.0037 g of alkali lignin and 0.5044 g of catalyst were placed in a 100 mL autoclave, and then 30 mL of anhydrous ethanol was added, and sufficiently mixed in an ultrasonic vibrator. Subsequently, 0.5 MPa high-purity nitrogen was introduced. Before reaction, the mixture was stirred for 15 minutes at 380 rpm, and then heated from 25° C. normal temperature to 280° C. at a temperature rising rate of 6° C./min, and the reaction was carried out at this temperature for 4 hours. After the reaction, the autoclave was quickly quenched in an ice water bath. After the temperature was lowered to normal temperature, the autoclave was opened and the reaction product was removed. The reaction product was first filtered with a sand core funnel to separate the solid and liquid phases, and the solid phase product was washed repeatedly with anhydrous ethanol solvent. After multiple washings, the solid phase product was removed, and dried in a drying oven at 105° C. for 12 hours. The liquid phase product was placed in a rotary evaporator and dried by evaporation in a 100 mL distillation flask under the conditions of 44° C. and 110 r/min (to remove the ethanol solvent and water phase) to obtain 2-ethoxyphenol and co-product lignin oil in liquid state. According to calculations, the conversion rate of lignin was 97%, the selectivity of 2-ethoxyphenol among the phenolic monomers in the liquid product was 26%, and the yield was 115 mg/g of lignin.

EXAMPLE 6

Preparation of a Catalyst and Catalytic Depolymerization of Lignin to 2-Ethoxyphenol 0.94 g of ammonium tungstate was completely dissolved in 100 ml of deionized water, and 5 g of sepiolite prepared in the example was added. After stirring evenly, the mixture was vibrated in an ultrasonic vibrator for 1 hour, subsequently treated in a hydrothermal synthesis kettle at 180° C. for 20 hours, dried by evaporation at 90° C., and then dried at 105° C. for 12 hours. Thereafter, the obtained solids were ground into powder, calcined in a tube furnace at 500° C. for 4 hours under an air atmosphere, and collected, the heating rate being 2° C./min. The collected solid powder was added to an aqueous solution of 1.07 g of nickel nitrate and treated in the same way. After collection, it was impregnated with 0.65 g of ammonium molybdate in the same way to obtain a catalyst for preparing 2-ethoxyphenol by catalytic depolymerization of lignin with a total content of 20 wt % of tungsten, nickel and molybdenum.

1.0058 g of alkali lignin and 0.5012 g of catalyst were placed in a 100 mL autoclave, and then 30 mL of anhydrous ethanol was added, and sufficiently mixed in an ultrasonic vibrator. Subsequently, 0.5 MPa high-purity nitrogen was introduced. Before reaction, the mixture was stirred for 15 minutes at 380 rpm, and then heated from 25° C. normal temperature to 300° C. at a temperature rising rate of 6° C./min, and the reaction was carried out at this temperature for 5 hours. After the reaction, the autoclave was quickly quenched in an ice water bath. After the temperature was lowered to normal temperature, the autoclave was opened and the reaction product was removed. The reaction product was first filtered with a sand core funnel to separate the solid and liquid phases, and the solid phase product was washed repeatedly with anhydrous ethanol solvent. After multiple washings, the solid phase product was removed, and dried in a drying oven at 105° C. for 12 hours. The liquid phase product was placed in a rotary evaporator and dried by evaporation in a 100 mL distillation flask under the conditions of 44° C. and 110 r/min (to remove the ethanol solvent and water phase) to obtain 2-ethoxyphenol and co-product lignin oil in liquid state. According to calculations, the conversion rate of lignin was 95%, the selectivity of 2-ethoxyphenol among the phenolic monomers in the liquid product was 20%, and the yield was 100 mg/g of lignin.

EXAMPLE 7

Preparation of a Catalyst and Catalytic Depolymerization of Lignin to 2-Ethoxyphenol 1.25 g of ammonium tungstate was completely dissolved in 100 ml of deionized water, and 5 g of sepiolite prepared in the example was added. After stirring evenly, the mixture was vibrated in an ultrasonic vibrator for 1 hour, subsequently treated in a hydrothermal synthesis kettle at 180° C. for 20 hours, dried by evaporation at 90° C., and then dried at 105° C. for 12 hours. Thereafter, the obtained solids were ground into powder, calcined in a tube furnace at 500° C. for 4 hours under an air atmosphere, and collected, the heating rate being 2° C./min. The collected solid powder was added to an aqueous solution of 1.43 g of nickel nitrate and treated in the same way. After collection, it was impregnated with 0.87 g of ammonium molybdate in the same way to obtain a catalyst for preparing 2-ethoxyphenol by catalytic depolymerization of lignin with a total content of 25 wt % of tungsten, nickel and molybdenum.

1.0052 g of alkali lignin and 0.5062 g of catalyst were placed in a 100 mL autoclave, and then 30 mL of anhydrous ethanol was added, and sufficiently mixed in an ultrasonic vibrator. Subsequently, 0.5 MPa high-purity nitrogen was introduced. Before reaction, the mixture was stirred for 15 minutes at 380 rpm, and then heated from 25° C. normal temperature to 280° C. at a temperature rising rate of 6° C./min, and the reaction was carried out at this temperature for 4 hours. After the reaction, the autoclave was quickly quenched in an ice water bath. After the temperature was lowered to normal temperature, the autoclave was opened and the reaction product was removed. The reaction product was first filtered with a sand core funnel to separate the solid and liquid phases, and the solid phase product was washed repeatedly with anhydrous ethanol solvent. After multiple washings, the solid phase product was removed, and dried in a drying oven at 105° C. for 12 hours. The liquid phase product was placed in a rotary evaporator and dried by evaporation in a 100 mL distillation flask under the conditions of 44° C. and 110 r/min (to remove the ethanol solvent and water phase) to obtain 2-ethoxyphenol and co-product lignin oil in liquid state. According to calculations, the conversion rate of lignin was 96%, the selectivity of 2-ethoxyphenol among the phenolic monomers in the liquid product was 23%, and the yield was 107 mg/g of lignin.

EXAMPLE 8

Preparation of a Catalyst and Catalytic Depolymerization of Lignin to 2-Ethoxyphenol 1.61 g of ammonium tungstate was completely dissolved in 100 ml of deionized water, and 5 g of sepiolite prepared in the example was added. After stirring evenly, the mixture was vibrated in an ultrasonic vibrator for 1 hour, subsequently treated in a hydrothermal synthesis kettle at 180° C. for 20 hours, dried by evaporation at 90° C., and then dried at 105° C. for 12 hours. Thereafter, the obtained solids were ground into powder, calcined in a tube furnace at 500° C. for 4 hours under an air atmosphere, and collected, the heating rate being 2° C./min. The collected solid powder was added to an aqueous solution of 1.84 g of nickel nitrate and treated in the same way. After collection, it was impregnated with 1.12 g of ammonium molybdate in the same way to obtain a catalyst for preparing 2-ethoxyphenol by catalytic depolymerization of lignin with a total content of 30 wt % of tungsten, nickel and molybdenum.

1.0038 g of alkali lignin and 0.5074 g of catalyst were placed in a 100 mL autoclave, and then 30 mL of anhydrous ethanol was added, and sufficiently mixed in an ultrasonic vibrator. Subsequently, 0.5 MPa high-purity nitrogen was introduced. Before reaction, the mixture was stirred for 15 minutes at 380 rpm, and then heated from 25° C. normal temperature to 280° C. at a temperature rising rate of 6° C./min, and the reaction was carried out at this temperature for 2 hours. After the reaction, the autoclave was quickly quenched in an ice water bath. After the temperature was lowered to normal temperature, the autoclave was opened and the reaction product was removed. The reaction product was first filtered with a sand core funnel to separate the solid and liquid phases, and the solid phase product was washed repeatedly with anhydrous ethanol solvent. After multiple washings, the solid phase product was removed, and dried in a drying oven at 105° C. for 12 hours. The liquid phase product was placed in a rotary evaporator and dried by evaporation in a 100 mL distillation flask under the conditions of 44° C. and 110 r/min (to remove the ethanol solvent and water phase) to obtain 2-ethoxyphenol and co-product lignin oil in liquid state. According to calculations, the conversion rate of lignin was 97%, the selectivity of 2-ethoxyphenol among the phenolic monomers in the liquid product was 24%, and the yield was 112 mg/g of lignin.

EXAMPLE 9

Preparation of a Catalyst and Catalytic Depolymerization of Lignin to 2-Ethoxyphenol 2.03 g of ammonium tungstate was completely dissolved in 100 ml of deionized water, and 5 g of sepiolite prepared in the example was added. After stirring evenly, the mixture was vibrated in an ultrasonic vibrator for 1 hour, subsequently treated in a hydrothermal synthesis kettle at 180° C. for 20 hours, dried by evaporation at 90° C., and then dried at 105° C. for 12 hours. Thereafter, the obtained solids were ground into powder, calcined in a tube furnace at 500° C. for 4 hours under an air atmosphere, and collected, the heating rate being 2° C./min. The collected solid powder was added to an aqueous solution of 2.31 g of nickel nitrate and treated in the same way. After collection, it was impregnated with 1.41 g of ammonium molybdate in the same way to obtain a catalyst for preparing 2-ethoxyphenol by catalytic depolymerization of lignin with a total content of 35 wt % of tungsten, nickel and molybdenum.

1.0028 g of alkali lignin and 0.5033 g of catalyst were placed in a 100 mL autoclave, and then 30 mL of anhydrous ethanol was added, and sufficiently mixed in an ultrasonic vibrator. Subsequently, 0.5 MPa high-purity nitrogen was introduced. Before reaction, the mixture was stirred for 15 minutes at 380 rpm, and then heated from 25° C. normal temperature to 280° C. at a temperature rising rate of 6° C./min, and the reaction was carried out at this temperature for 5 hours. After the reaction, the autoclave was quickly quenched in an ice water bath. After the temperature was lowered to normal temperature, the autoclave was opened and the reaction product was removed. The reaction product was first filtered with a sand core funnel to separate the solid and liquid phases, and the solid phase product was washed repeatedly with anhydrous ethanol solvent. After multiple washings, the solid phase product was removed, and dried in a drying oven at 105° C. for 12 hours. The liquid phase product was placed in a rotary evaporator and dried by evaporation in a 100 mL distillation flask under the conditions of 44° C. and 110 r/min (to remove the ethanol solvent and water phase) to obtain 2-ethoxyphenol and co-product lignin oil in liquid state. According to calculations, the conversion rate of lignin was 98%, the selectivity of 2-ethoxyphenol among the phenolic monomers in the liquid product was 25%, and the yield was 116 mg/g of lignin.

EXAMPLE 10

Structure Determination of the Catalyst

The structural characteristics of the catalyst as prepared in Example 2 for catalytic depolymerization of lignin to 2-ethoxyphenol were studied through various characterizations. The results are as follows:

As shown in FIG. 1, the specific surface area, pore volume, and pore diameter of the catalyst were analyzed by the $N_2$-adsorption-desorption test method. The catalyst exhibited typical mesoporous structure characteristics with a relatively high specific surface area, which is beneficial to the adsorption of the reaction substrate and promotes the proceeding of the depolymerization reaction.

Figure 2:
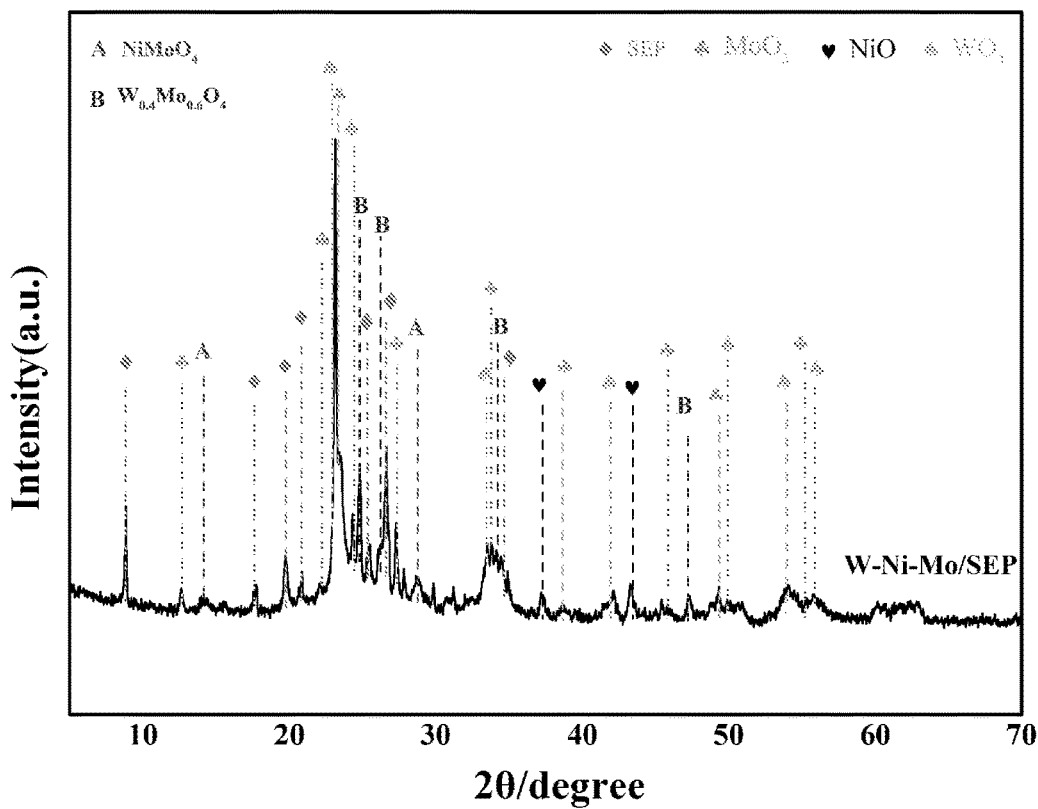
FIG. 2 is a diagram showing the X-ray diffraction analysis of the catalyst prepared in Example 2 of the present disclosure.

As shown in FIG. 2, the crystal structure and components on the catalyst surface were analyzed by XRD. The characteristic diffraction peak corresponding to SEP was detected, and it can be that the original SEP carrier structure is retained after the introduction of metals. Among these, the oxidation state crystal phases ($WO_3$, NiO, $MoO_3$) corresponding to the three metals W, Ni and Mo were detected, respectively, indicating that in the three-metal catalyst, the active metals mainly existed in the oxidation state, and also proving the successful introduction of the active metals. The active metal sites can activate hydrogen atoms and promote hydrogenolysis of the β-O-4 bond of lignin. In addition, the presence of alloy phases (W0.4Mo0.6O4, NiMoO4) between the metals was also detected, proving that there was an electronic exchange between the metals and a strong interaction occurred. The formation of the alloy phases is conducive to the improvement of the catalyst's stability and adsorption towards the reaction substrate, and enhances the catalyst's recycling property and selectivity for depolymerization of lignin.

Figure 3:
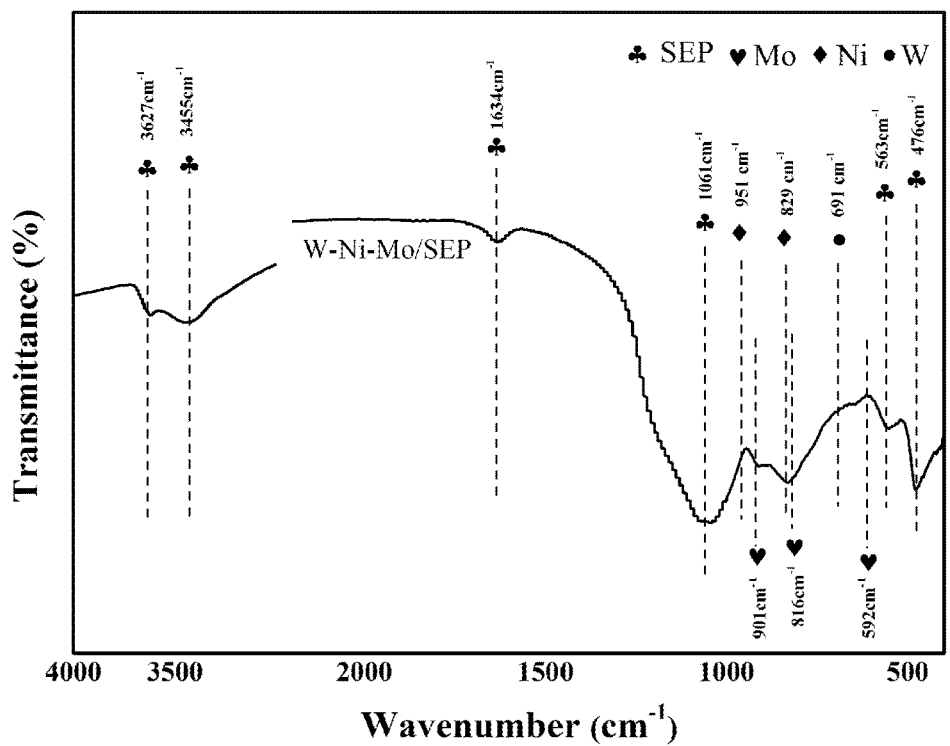
FIG. 3 is a diagram showing the Fourier Transform Infrared Spectroscopy study of the catalyst prepared in Example 2 of the present disclosure.

As shown in FIG. 3, the properties of the groups on the catalyst surface were analyzed by FTIR spectroscopy, proving the existence of hydroxyl (O—H) bonds, Si—O bonds, and Si—O—Si/Al bonds in the SEP. In addition, other absorption bands were attributed to the stretching vibration of Mo═O double bonds, Mo—O single bonds, Mo—O—Mo bonds in the active Mo metal oxide, and the vibration of O—W—O bonds and Ni—O in the W and Ni metal oxides. It was proven that there were abundant oxygen species on the surface of the catalyst, which showed good adsorption and selectivity to the reactants.

Figure 4:
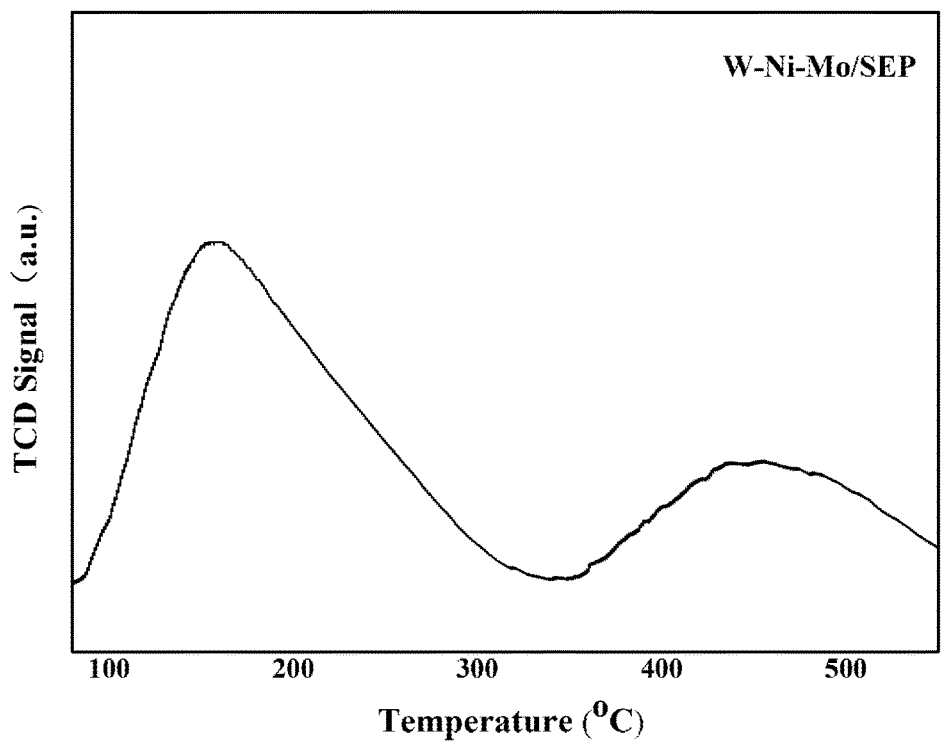
FIG. 4 is a diagram showing the $NH_3$-TPD study of the catalyst prepared in Example 2 of the present disclosure.
Figure 5:
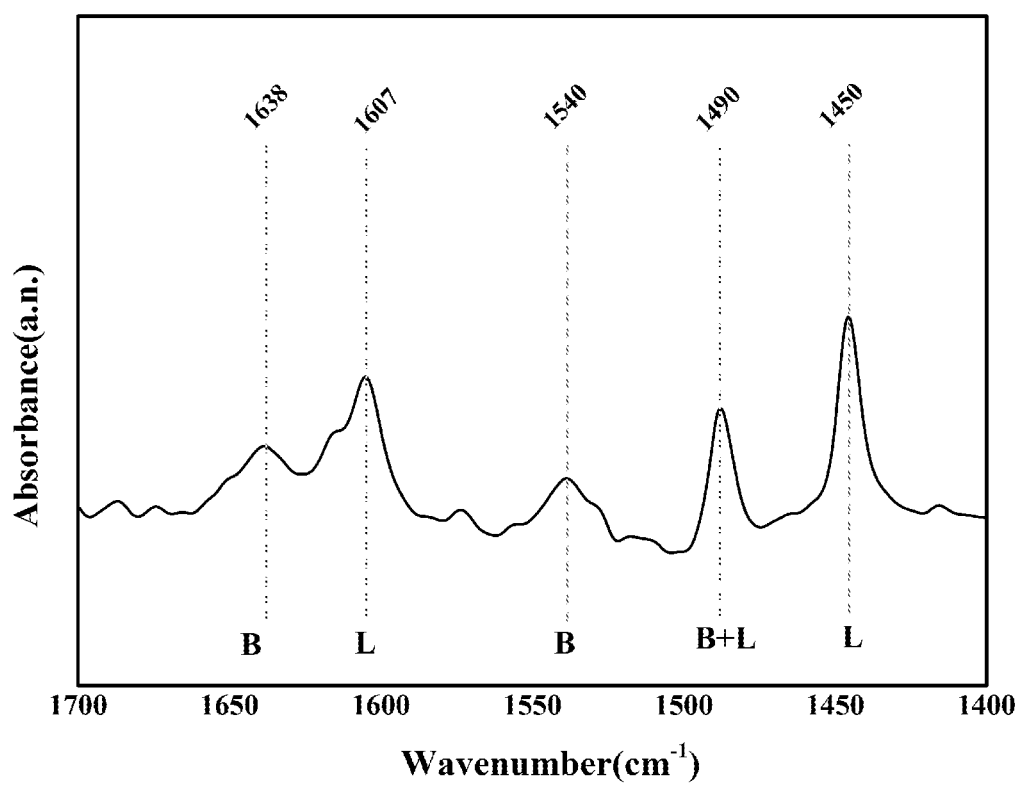
FIG. 5 is a diagram showing the Py-IR study of the catalyst prepared in Example 2 of the present disclosure.

As shown in FIGS. 4 and 5, the surface acidity of the catalyst was analyzed by NH3-TPD and Py-IR. It can be seen that the catalyst mainly has weak acid sites and strong acid sites. The surface acid sites of the catalyst have an important influence on the catalytic behavior of lignin depolymerization. In addition, the catalyst exhibits abundant Brønsted acid and Lewis acid sites. Studies have shown that Lewis acid sites can effectively break the C—O bond in lignin, and Brönsted acid sites can catalyze alkylation and isomerization reactions of intermediates of lignin depolymerization. Based on the synergistic effect between the active metal sites and the acid sites, a highly selective cleavage of lignin β-O-4 bond is first carried out, and then the reaction intermediates are further alkylated and isomerized to produce 2-ethoxyphenol with a high selectivity.

It should be understood that the examples and embodiments described herein are for illustrative purposes only and are not intended to limit the present disclosure. A person skilled in the art can make various modifications or changes based on them. Anything made within the spirit and principle of the present disclosure. Any modifications, equivalent replacements, improvements, and the like should all be included in the protection scope of the present disclosure.

What is claimed is:

1. A method for preparing 2-ethoxyphenol by catalytic depolymerization of lignin, comprising the following steps:
   using ethanol as a reaction medium, adding lignin and a catalyst to ethanol to obtain a reactant, and subjecting the reactant to a reaction in a $N_2$ atmosphere;
   wherein the catalyst comprises the following components:
   a sepiolite as a carrier, and tungsten, nickel, and molybdenum as active components supported on the sepiolite, wherein
   a molar ratio of the tungsten, the nickel, and the molybdenum is in a range of 0.6-0.9:1:0.6-1.5; and
   a total content of the tungsten, the nickel and the molybdenum is 20 to 40 wt % of the catalyst.

2. The method for preparing 2-ethoxyphenol by catalytic depolymerization of lignin according to claim 1, wherein the lignin, the catalyst and the ethanol are fed in a mass ratio of 0.8 to 1.2:0.3 to 0.7:28 to 32.

3. The method for preparing 2-ethoxyphenol by catalytic depolymerization of lignin according to claim 1, wherein the reaction is carried out at a temperature of 260 to 300° C., a pressure of 6.2 to 9.5 MPa and a stirring rate of 350 to 550 r/min for 1 to 5 hours.

4. The method for preparing 2-ethoxyphenol by catalytic depolymerization of lignin according to claim 1, wherein the method further comprises the following steps: selecting a precursor salt of the tungsten, a precursor salt of the nickel, and a precursor salt of the molybdenum; and loading the tungsten, the nickel and the molybdenum on the sepiolite by a stepwise impregnation method in the order of tungsten impregnation, nickel impregnation and molybdenum impregnation to obtain the catalyst for preparing 2-ethoxyphenol by catalytic depolymerization of lignin.

5. The method for preparing 2-ethoxyphenol by catalytic depolymerization of lignin according to claim 4, wherein a hydrothermal assistant aging treatment is used in the impregnation treatment processes, and wherein the hydrothermal assistant aging treatment is an airtight and constant-temperature treatment in a high-pressure hydrothermal synthesis kettle, which is carried out under a $N_2$ atmosphere, at a temperature of 80 to 180° C., and for a time of 12 to 24 hours.

6. The method for preparing 2-ethoxyphenol by catalytic depolymerization of lignin according to claim 2, wherein the reaction is carried out at a temperature of 260 to 300° C., a pressure of 6.2 to 9.5 MPa and a stirring rate of 350 to 550 r/min for 1 to 5 hours.

* * * * *